United States Patent [19]

Lewis et al.

[11] Patent Number: 5,394,875
[45] Date of Patent: Mar. 7, 1995

[54] AUTOMATIC ULTRASONIC LOCALIZATION OF TARGETS IMPLANTED IN A PORTION OF THE ANATOMY

[76] Inventors: Judith T. Lewis, 855 Glendale La., Nashville, Tenn. 37204; Robert L. Galloway, Jr., 7736 Indian Springs Dr., Nashville, Tenn. 37221

[21] Appl. No.: 139,139

[22] Filed: Oct. 21, 1993

[51] Int. Cl.$^6$ .............................................. A61B 8/00
[52] U.S. Cl. ........................... 128/660.09; 128/916
[58] Field of Search ................... 128/660.01, 662.02, 128/662.05, 660.09, 916, 653.1

[56] References Cited

U.S. PATENT DOCUMENTS

| | | | |
|---|---|---|---|
| 4,316,391 | 2/1982 | Tickner | 128/662.02 |
| 4,373,532 | 2/1983 | Hill et al. | 128/662.02 |
| 4,932,414 | 6/1990 | Coleman et al. | 128/916 |
| 5,161,536 | 11/1992 | Vilkomersn et al. | 128/662.05 |
| 5,167,165 | 12/1992 | Brucher et al. | 128/660.09 |

*Primary Examiner*—George Manuel
*Attorney, Agent, or Firm*—Kenyon & Kenyon

[57] ABSTRACT

In a coordinate system defined by a coordinate space digitizer, the location of an implanted symmetric object may automatically be determined based on differences between the characteristic acoustic impedances of at least a portion of an implanted object and one or more materials surrounding that object. An A-mode ultrasound transducer may be attached to a coordinate space digitizer or pointing device such that an attached computer tracks the position and orientation of the ultrasound transducer. The reflected radio-frequency (rf) ultrasound signals may automatically be analyzed along with the transducer position and orientation corresponding to each received rf signal to detect the position of the implanted object. The time delay between received ultrasound echoes is used to compute the depth of the object from the transducer. This allows for an accurate determination of the three-dimensional coordinates of the implanted object.

80 Claims, 11 Drawing Sheets

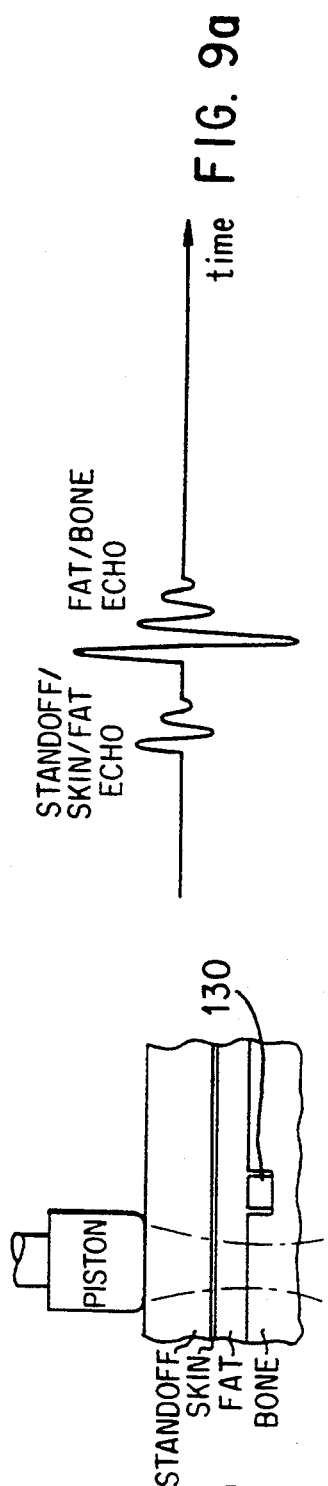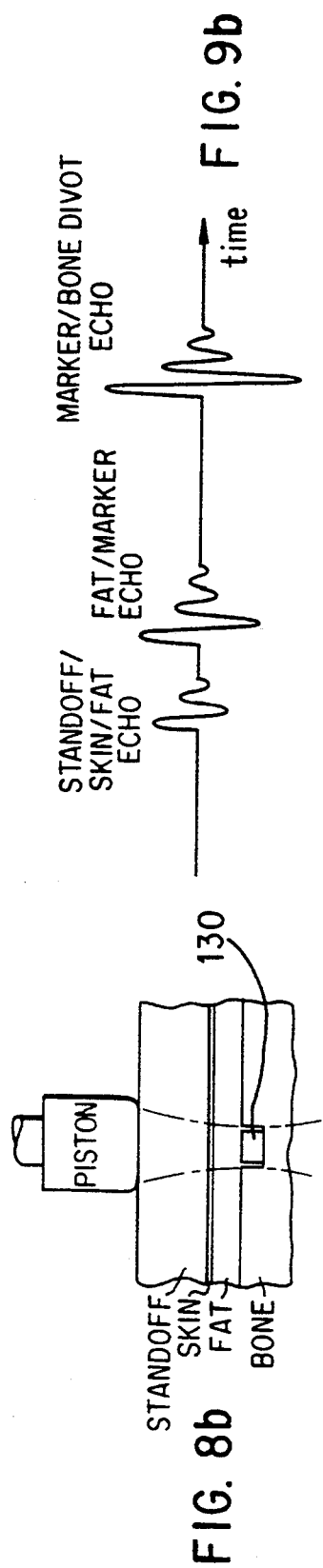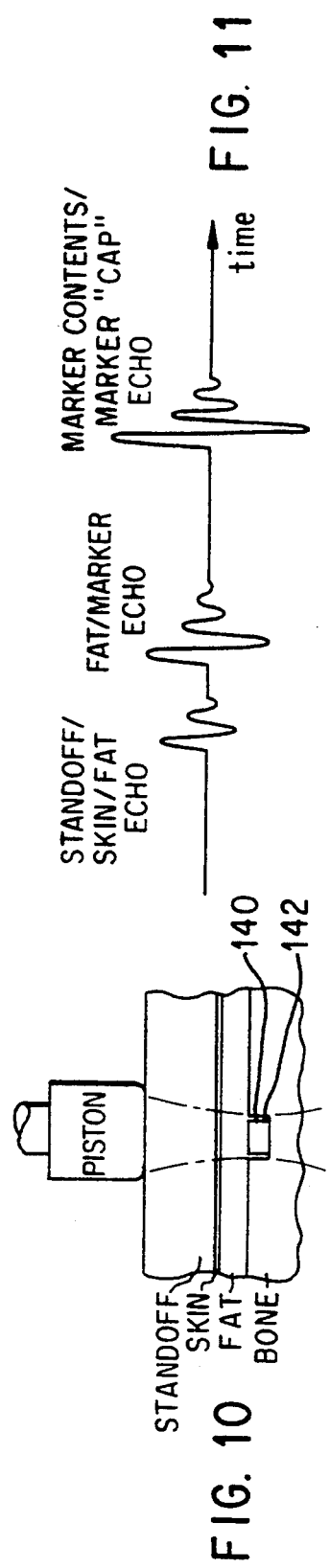

AUTOMATIC ULTRASONIC LOCALIZATION OF TARGETS IMPLANTED IN A PORTION OF THE ANATOMY

BACKGROUND OF THE INVENTION

The present invention relates to locating a position of an object implanted in a portion of the anatomy, the object having at least a portion which is in a vicinity of a material having a different acoustic impedance than an acoustic impedance of that portion of the object. More particularly, the present invention relates to the localization of implanted targets using amplitude-mode (A-mode) ultrasound techniques and a coordinate space digitizer. Extendable to other applications, the automatic implanted target localization approach may be used to locate small fluid-filled polymer cylinders implanted in human skull, which are preferably flush with the surface of the skull, beneath the scalp and subcutaneous fat. These permanently-implanted cylinders are intended to serve as fiducial markers for the registration of tomographic image volumes with physical space in neurosurgical cases, as well as for tracking a patient over time.

Tomographic imaging modalities, such as computer tomography (CT), magnetic resonance imaging (MRI), and positron emission tomography (PET), produce a three-dimensional image volume as a set of three-dimensional "slices". These image volumes contain the information necessary for surgical or radiotherapeutic planning. Such information may include the three-dimensional distances between sites of interest such as tumors, the location of blood vessels which must be avoided, and lesion margin delineation often superior to that discernible by visual tissue inspection.

However, these three-dimensional volumes are at an arbitrary orientation to each other as well as to the physical patient anatomy. As a result, correlating and comparing the same location in the images is difficult. Also, the surgeon is unable to accurately correlate the detailed image information with the physical anatomy during surgery as a guidance tool.

The correlation of multiple three-dimensional volumes or spaces is referred to as space registration. Space registration establishes a one-to-one mapping between points in the image sets or between points in one or more image sets and physical space. The transformation between coordinate systems is calculated based on the location of a set of at least three common landmarks, or fiducial markers, in each representation. The actual fiducial point is the geometric center of the fiducial marker. The accuracy of the mapping between coordinate systems depends on the accuracy with which the coordinates of the fiducial markers centers are known in each three-dimensional space.

The fiducial markers provide a frame of reference to make image-to-image or image-to-physical space registration possible. A general technique for using fiducial markers to obtain registration of image data across time is set forth in U.S. Pat. No. 4,991,579 to Allen et al., which is incorporated herein by reference.

Fiducial markers for accurate image-to-physical space registration must be rigidly located and must be composed of materials making them visible in the imaging modalities of interest. U.S. patent application Ser. No. 08/017,167 to McCrory et al., which is incorporated herein by reference, describes the design and composition of fiducial markers for neurosurgical image registration and image-physical space registration, as well as a method for localizing the center of the imaged markers in the image volumes. This patent application describes two types of markers including temporary markers anchored in the skull for rigidity but with the image-visible portion protruding above the scalp, and permanent markers implanted into the skull beneath the scalp and subcutaneous fat.

Internal permanent fiducial markers allow the comparison of images over time for follow-up therapy. Permanent markers also allow the delivery of fractionated radiotherapy, in which small doses of radiation are administered in multiple sessions to maximize the dose delivered to the target lesion while minimizing the damage to surrounding tissue. Fractionated radiotherapy requires the same fiducial framework to be present, in an unchanged position, for each treatment so that the radiation beam may be properly directed relative to the fiducial markers as determined from the pre-treatment images. Temporary markers and stereotactic frames can neither remain in position long enough nor be re-affixed accurately to satisfy this requirement.

In addition to a fiducial marking approach, image-to-physical space registration requires a method for establishing the coordinate system in physical space. Several coordinate space digitizers including specific pointing devices have been developed which define a coordinate space and pass the three-dimensional coordinates of the endpoint to an attached computer. As an example, an articulated arm has joints that track the angular position of each link, allowing the attached computer to calculate the endpoint coordinates. A less cumbersome alternative is a wand with infrared light emitting diodes (LEDs) along its shaft in which the LEDs are strobed in sequence and an infrared camera attached to a computer notes the location of the LEDs relative to a set of reference LEDs in a fixed position.

Also required of a system which correlates neurological image space and physical space is a means for locating the center of the fiducial markers in the coordinate system defined by the pointing device. For markers visible outside the scalp, the fiducial position can be recorded simply by touching the fiducial marker with the pointing device. For permanent, subcutaneously-implanted markers, however, locating the precise three-dimensional position of the marker is much more challenging. A target localization method to address this task has previously become necessary in the field of registration of image volumes with physical space in neurosurgical cases.

Once the markers have been located in the preoperative image sets stored on a computer as well as in the physical space defined by a pointing device attached to the same computer, the system display can provide interactive surgical guidance. The location of the endpoint of the pointing device is indicated on a display of the appropriate slice through the image volumes. Such an interactive, image-guided surgery system using an articulated arm as a pointing device is described in U.S. Pat. No. 5,142,930 to Allen et al., which is incorporated herein by reference.

U.S. Pat. No. 5,197,476 to Nowacki et al., which is also incorporated herein by reference, discloses an ultrasound probe coupled with an infrared LED-based pointing device to locate a target in a living body. A three-dimensional frame containing a plurality of infrared lights is placed on a table. A computer strobes the infrared lights and the position of the infrared lights is monitored by a pair of infrared sensitive cameras and stored in the computer. A hand held ultrasonic probe is provided with a plurality of infrared lights so that the probe can be monitored by the cameras. The computer compares the positions of the probe lights with the initial position of the frame infrared lights to accurately determine the position of the probe so that the position of the target in the body may be displayed on a computer monitor. The approach disclosed in the Nowacki et al. patent employs a brightness-mode (B-mode) ultrasound imaging and requires a trained expert to visually recognize when the desired target is displayed.

SUMMARY OF THE INVENTION

The present invention relates to a method and apparatus for automatically localizing the three-dimensional coordinates of a symmetrically-shaped implanted target. The ultrasonic method is based on differences in the characteristic acoustic impedance ($Z_0$) of the target and that of the surrounding material or surrounding materials as well as on the time delays between ultrasonic echoes.

The present invention uses A-mode ultrasound which produces one-dimensional, time domain "signals". Echoes received by the transducer are indicated as deflections in the signal and the amplitude of these deflections is proportional to the difference in acoustic impedances of the materials which form the interface from which the echo arose. In contrast, B-mode ultrasound imaging produces a two-dimensional image such as that provided on a video display, where each displayed line of the image corresponds to a single A-mode signal acquired from adjacent positions. The brightness or intensity of each pixel or dot along that line corresponds to the amplitude of received echoes.

According to an embodiment of the present invention, an A-mode ultrasonic transducer is attached to a pointing device which digitizes the coordinates of physical space. The automatic target detection algorithm is implemented on a computer that receives the reflected ultrasound signals along with the transducer position and orientation information. A position of the target or fiducial marker in a coordinate system of the pointing device is determined in response to the received echoes and the position and orientation of the transducer.

The present invention is based on the following ultrasonic principles. When an ultrasonic pulse is emitted from a transducer, it propagates through a material until it reaches an interface with a material of different characteristic acoustic impedance. At this interface, a portion of the power of the pulse is reflected back to be received by the transducer and the remainder propagates on to deeper interfaces. The ratio of reflected to transmitted power is proportional to the square of the difference in the characteristic acoustic impedances of the two materials. The time delay between the echoes received by the transducer may be multiplied by the speed of sound in the intervening material to obtain the distance traveled by the ultrasonic pulse and the speed of sound in the intervening material.

The present invention provides accurate localization, appropriate for localizing the center of small targets such as those a few millimeters in diameter. Accuracy is critical for the described application of the invention to image-to-physical space registration. An example of a fiducial marker design for that application is a cylinder, 3 mm in diameter, 4 mm in height, consisting of a polymer shell and an aqueous solution. Such a marker would be implanted into the skull flush with the surface of the skull, beneath the skin and subcutaneous fat.

BRIEF DESCRIPTION OF THE DRAWINGS

Other features and advantages of the present invention will become apparent from the following description taken in conjunction with the attached drawings.

FIG. 6, which includes

FIG. 7, illustrate a correspondence between the positions illustrated in FIG. 6(a), FIG. 6(b) and FIG. 6(c) and corresponding received reflections including a target interface echo signal on which the automatic localization technique according to the present invention is based.

FIG. 8, which includes FIG. 8(a) and FIG. 8(b), illustrates a low-impedance implanted fiducial marker for a neurosurgical space registration application of the present invention.

FIG. 9, which includes FIG. 9(a) and FIG. 9(b), illustrates expected received signals for the relative positions of the transducer piston and the fiducial marker illustrated in FIG. 8(a) and 8(b), respectively.

FIG. 10 illustrates an embodiment of the present invention in which a low impedance fiducial marker with a high impedance layer is used.

FIG. 11 illustrates expected received signals for the relative positions of the transducer piston and the fiducial marker illustrated in FIG. 10.

DETAILED DESCRIPTION

According to an embodiment of the present invention, an A-mode ultrasound transducer possessing a rotationally-symmetric beam (for example, a circular, single-crystal piston transducer) is attached to a pointing device such that the connected computer may track the coordinates and orientation of the transducer as the transducer is moved through space.

Figure 1:
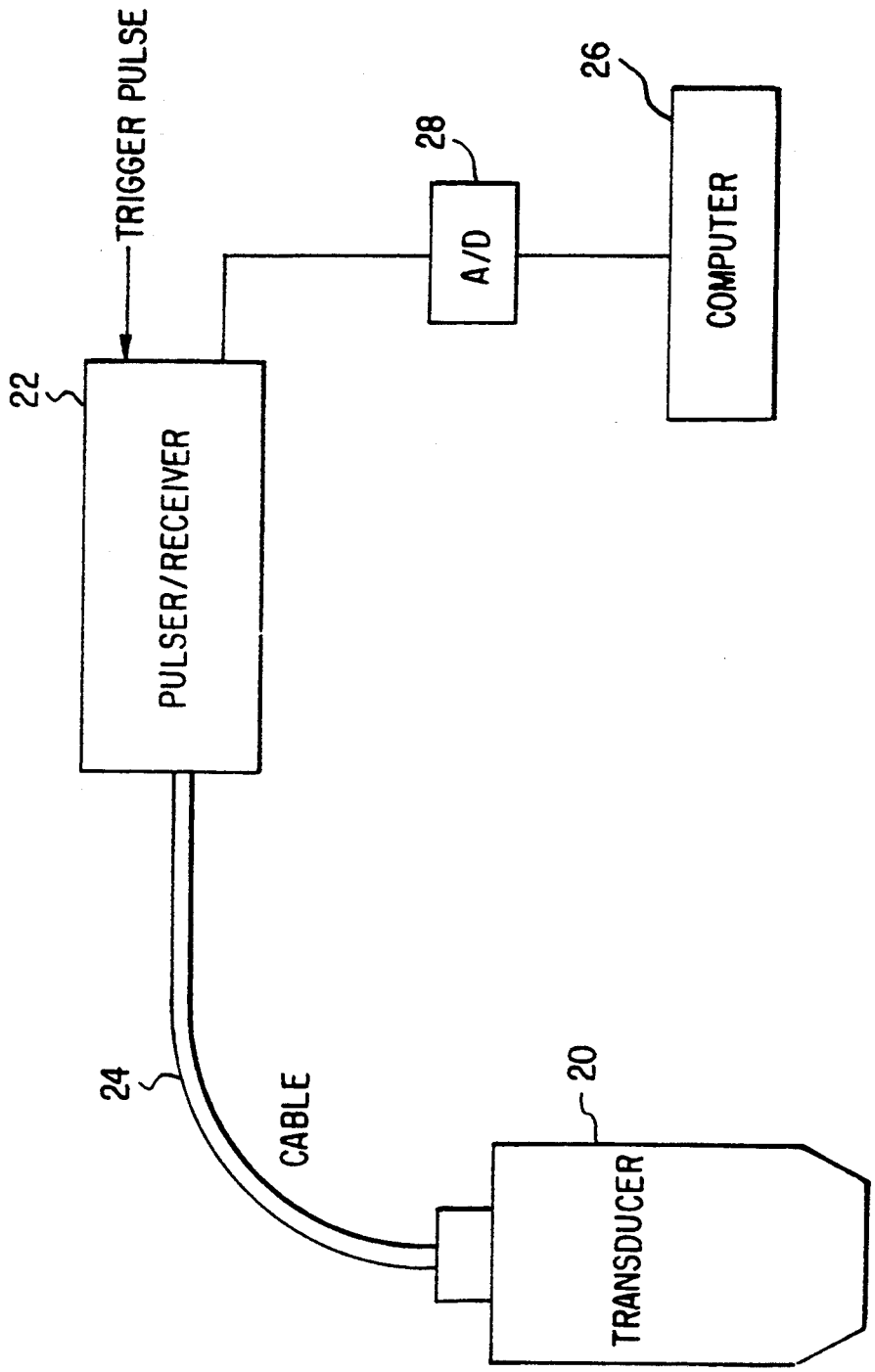
FIG. 1 illustrates an A-mode ultrasound transducer arranged with associated hardware according to an embodiment of the present invention.

FIG. 1 illustrates an example of an A-mode ultrasound transducer 20 with a beam (not illustrated) having a circular cross-section. In response to a trigger pulse, a pulser/receiver 22 provides an electrical trigger signal to the transducer 20 via a cable 24. In response to the electrical trigger signal transducer 20 emits an ultrasonic pulse. The transducer 20 then receives reflected acoustic waves and converts them to electrical time-domain signals, passing them to the pulser/receiver 22 via cable 24. These signals may be transferred to a computer 26 via an analog-to-digital (A/D) converter 28. The trigger pulse signal input to pulser/receiver 22 may be provided by computer 26.

According to an embodiment of the present invention, an operator translates the transducer 20 along a surface of interest perpendicular to the surface and with the aid of a coupling medium, such as water, acoustic scanning gel, or mineral oil. The computer 26 pulses the transducer 20 via pulser/receiver 22 and receives the reflected echoes along with the corresponding transducer location and orientation as determined by the pointing device system. As the emitted acoustic waves travel through layers of material with similar characteristic acoustic impedances ($Z_0$), little power is reflected back to the transducer 20. As a result those received echoes have a small amplitude.

When the ultrasound beam reaches an interface with an object whose acoustic impedance $Z_0$ is much different, a larger-amplitude echo results. Therefore, if an implanted target is composed of a material with an acoustic impedance $Z_0$ that is much greater or much less than the layers above or below it, a "target interface echo" will result. If enough prior knowledge exists to ensure that no other similar reflectors can be located in the expected depth range of the imbedded target, then the target can be automatically detected according to the present invention based on the presence of such a target interface echo.

The amplitude of the target interface echo will be a maximum when the largest portion of the ultrasound beam reaches and is reflected from that interface. If the ultrasound beam has a diameter greater than or approximately the same as the diameter of the target, the maximum echo amplitude occurs when the transducer is centered over the target. This theory, coupled with the position of the transducer corresponding to each received signal, may be used to map out the position of the target in the lateral plane, the plane perpendicular to the ultrasound beam. To then determine the depth of the target from the transducer face, the present invention detects the time delay between received echoes. Based on the knowledge of the speed of sound in the intervening materials, the direction of the transducer's orientation may be extrapolated along to estimate the three-dimensional location of the target.

Figure 2:
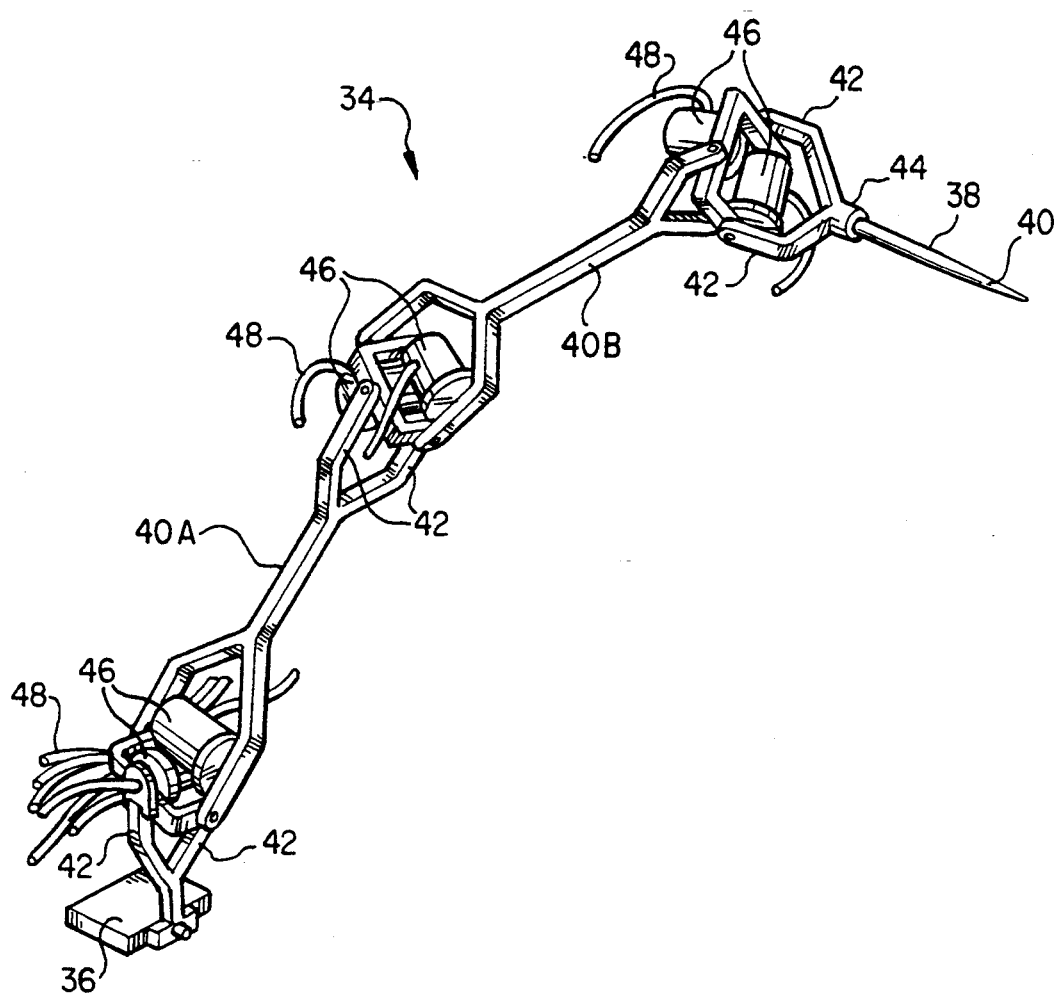
FIG. 2 is a mechanical articulated arm which may be used as a pointing device in an image-guided neurosurgery system.

One example of a pointing device which may be used to implement an embodiment of the present invention is an articulated arm employing encoders at each joint which track the angles between the arm's segments. FIG. 2 illustrates an example of such a pointing device system to which an ultrasound transducer may be attached according to an embodiment of the present invention. FIG. 2 illustrates an articulated arm 34 such as that used in the interactive, image-guided neurosurgery system described in U.S. Pat. No. 5,142,930 to Allen et al. As illustrated in FIG. 2, an external arm 34 is fixed to a base 36, which is movably fixed to some location. The arm 34 carries a tool 38 including an end tip 40 which is changeable and, for purposes of the present invention, is a pointing device which may include an attached ultrasound unit. A sensor (not illustrated in FIG. 2) which comprises an ultrasonic detector may be attached in place of the tool 38 and the end tip 40 of the tool 38 in order to practice the present invention. The arm 34 has two arm lengths 40A, 40B. The first arm length 40A is coupled to the base by two gimbal joints 42. The first arm length 40A therefore has two degrees of motion, as provided by the two gimbal joints 42.

A second arm length 40B is coupled to the first arm length 40A by a second pair of gimbal joints 42. The second pair of gimbal joints 42 provides the second arm length 40B with two additional degrees of motion. The second arm length 40B therefore has four degrees of motion relative to the base 36 of the arm 34.

A tool holder 44 is coupled to the second arm length 40B through a pair of gimbal joints 42. The tool holder 44 can hold any of a number of different tools, including a pointer, an ultrasound unit, a surgical laser, a biopsy probe, a radiation beam collimator, etc. In an embodiment of the present invention, the tool held by the tool holder 44 is an ultrasound unit (not illustrated in FIG. 2). A third pair of gimbal joints 42 provides the tool 38 with two additional degrees of motion, so that the tool 38 has 6 degrees of motion relative to the base 36.

The exact positioning of the tool 38 relative to the base 36 may be monitored by optical encoders 46. One optical encoder 46 is assigned to each gimbal joint 42. Each gimbal joint 42 is individually rotated around its pivot and the optical encoder 46 determines the precise amount of rotation of the gimbal joint 42 around its pivot. The information from each of the six optical encoders 46 is provided to a programmable computer (not illustrated in FIG. 2) via wires 48. The programmable computer can therefore precisely track the movement of the tool 38 relative to the base 36 by keeping track of the individual rotations of the gimbal joints 42 around their pivots.

Another example of a pointing device which may be used to implement the present invention uses infrared light emitting diodes (LEDs) along its shaft. The LEDs are strobed in sequence and an infrared camera attached to a computer notes the location of the LEDs relative to a set of reference LEDs in a fixed position. Such a system which digitizes the coordinates of physical space is the Optotrak/3020 (Northern Digital, Inc., Waterloo, Ontario), illustrated in FIG. 3. One implementation of this system is described in U.S. Pat. No. 5,197,476 issued to Nowacki et al.

Figure 3:
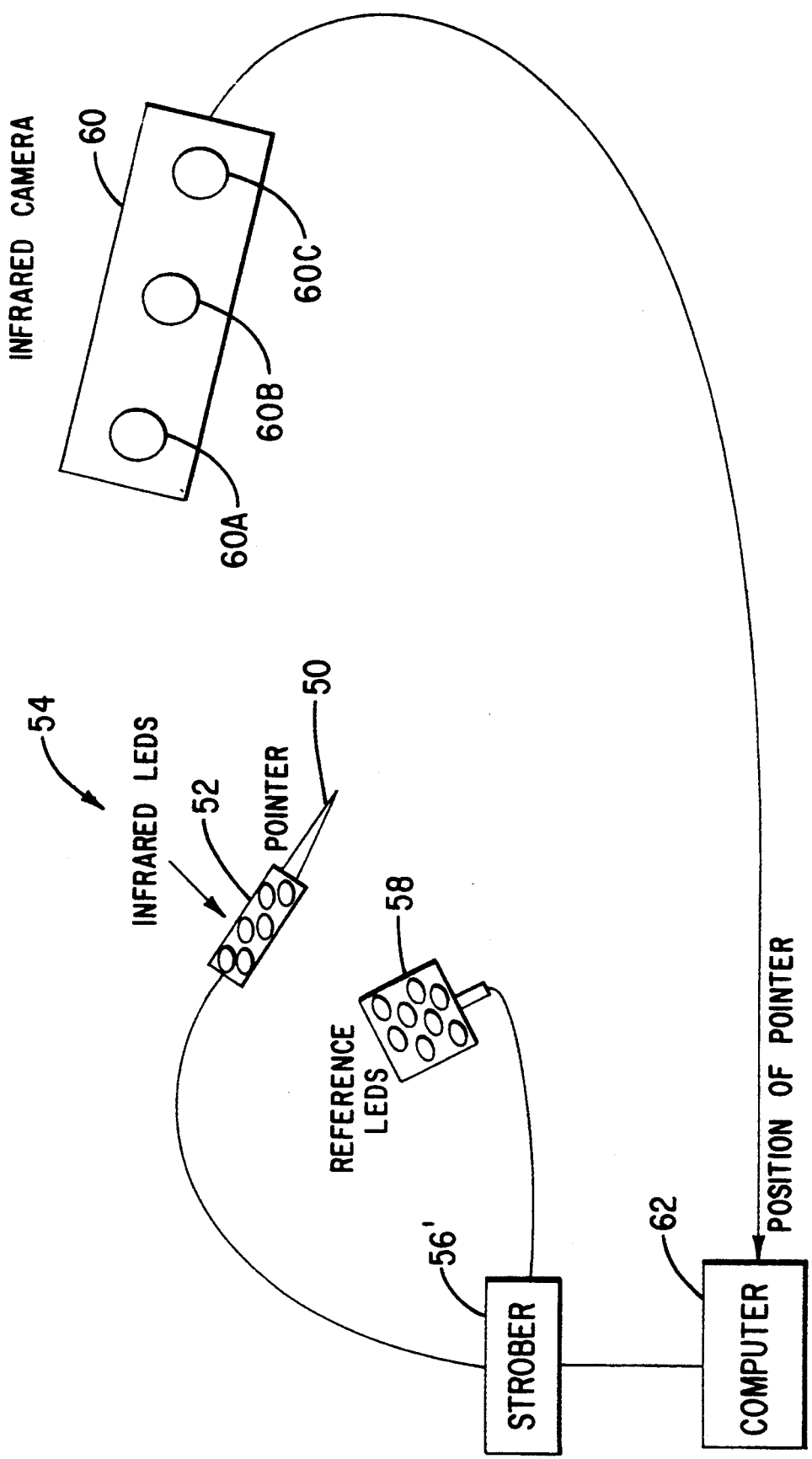
FIG. 3 is a schematic of the components of an optical pointing device system.

The optical system illustrated in FIG. 3 tracks the coordinates and orientation of an object 50 which is illustrated as a pointer, but may be replaced by an A-mode ultrasound transducer to implement an embodiment of the present invention. A shaft 52 extends from object 50 with a plurality of infrared light emitting diodes (LEDs) on its surface. A cable connects the probe 54 (consisting of shaft 52 and end-effector 50) to a strober 56. The probe 54 may be easily and freely manipulated by a user. Mounted in a fixed position near the region of interest is a set of reference infrared LEDs 58 referred to as a rigid body. This set of reference LEDs 58 establishes the origin of a three-dimensional coordinate system in physical space.

The infrared LEDs 52 and 58 are strobed in sequence by strober 56 and are visible to a position sensor 60.

Position sensor 60 includes three linear charge coupled device (CCD) cameras 60A, 60B, 60C with cylindrical optics placed in front of the CCDs to compress the field of view into a single line. The output of each CCD 60A, 60B, 60C is captured by a separate processor (not illustrated) which extracts the object's position in that view. A fourth processor (not illustrated) receives the output of each of the three separate individual processors and triangulates the location of an infrared LED and passes it to a computer 62. Since the infrared LEDs on the shaft 52 are pulsed in a known sequence and configuration, and the length of the end-effector 50 is known, the computer 62 is able to calculate the time-distinct location of the end-effector 50 with respect to the rigid body of reference infrared LEDs 58.

The present invention is not limited to embodiments of the present invention using the pointing devices illustrated in FIG. 2 and FIG. 3. In the present invention, an ultrasound transducer may be attached to any pointing device such that the coordinates and orientation of the transducer are continuously passed to the connected computer, as illustrated, for example, in FIG. 4.

Figure 4:
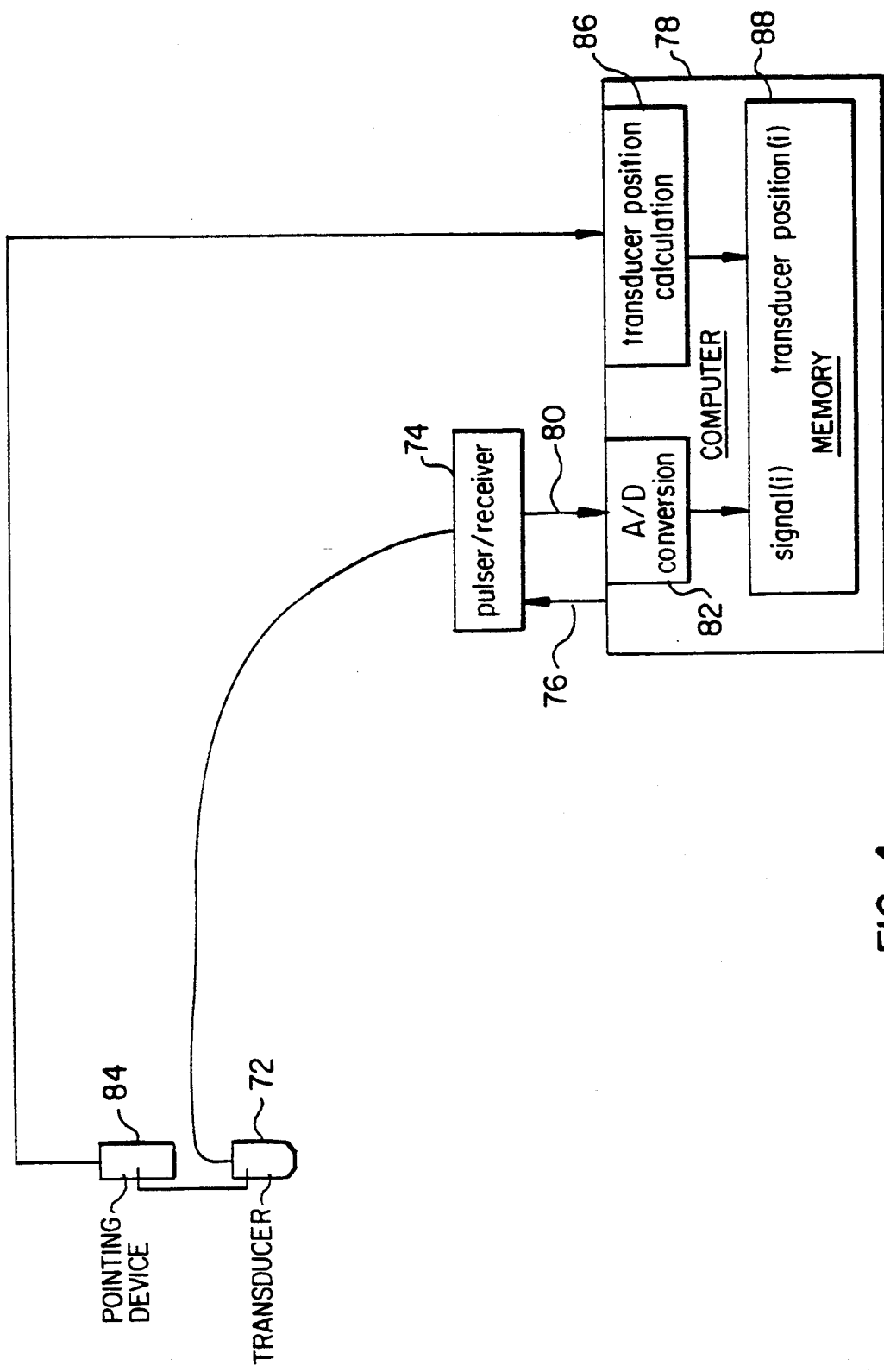
FIG. 4 illustrates the acquisition of signal and position information from an ultrasound transducer coupled to a pointing device according to an embodiment of the present invention.

In FIG. 4, each time a transducer 72 is pulsed by a pulser/receiver 74 in response to a trigger signal 76 from computer 78, an ultrasound signal 80 of specific time duration is acquired from pulser/receiver 74, digitized by an A/D converter 82 which may be included in computer 78, and stored as a signal (i) in a memory 88 of the computer 78. The rate at which the A/D converter 82 samples the analog ultrasound signal 80 must be sufficient to adequately represent the signal. The sampling frequency should be at least twice the frequency bandwidth of the ultrasound signal. Simultaneously, the position and orientation of the transducer 72 corresponding to the current signal are acquired from a pointing device 84. A transducer position calculator 86 calculates a transducer position (i) in response to the data provided from pointing device 84 which is stored in memory 88 along with the signal (i). In this manner, signal/position pairs are acquired while a region of an object or anatomy are scanned with the transducer assembly.

Figure 5:
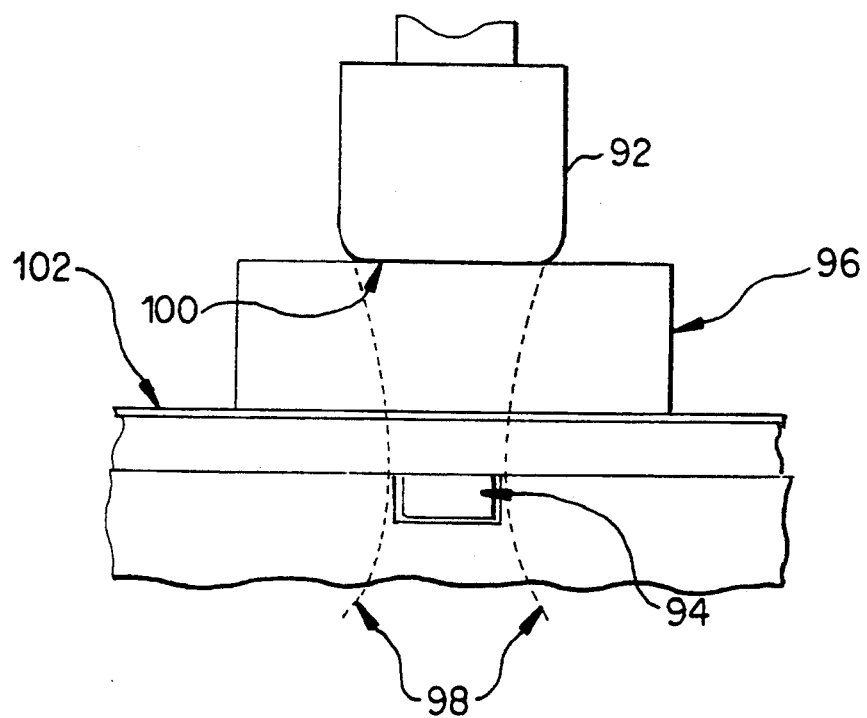
FIG. 5 illustrates a position of a transducer piston near a target and the use of an ultrasound standoff pad in placing the target in the optimal range of the ultrasound beam.

To gather signal/position pairs from an object or patient once that object or patient is secured in a fixed position, the transducer assembly is held by a user and moved across a surface of interest, keeping the transducer perpendicular to the surface. FIG. 5 illustrates a position of a transducer piston 92 near a target 94. An ultrasound stand-off pad 96 is used in placing the target 94 in an optimal range of an ultrasound beam 98 (illustrated by a dotted line) of the transducer piston 92. Contact between a transducer face 100 and the surface 102 is maintained with the aid of a coupling medium, such as acoustic gel or water. The ultrasonic stand-off pad 96 may be used to place the expected target depth in an optimal range of the ultrasound beam 98 depending on the expected depth of the implanted target 94 and the type of transducer used. Stand-off 96 may be a layer or "pad" of a gelatinous material or a water path.

Figure 7A:
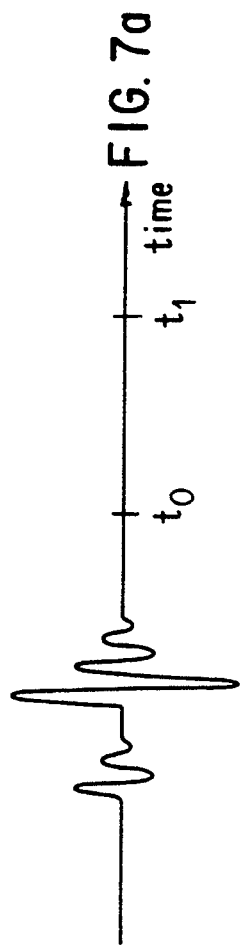
FIG. 7(a), FIG. 7(b) and FIG. 7(c), which together comprise
Figure 7B:
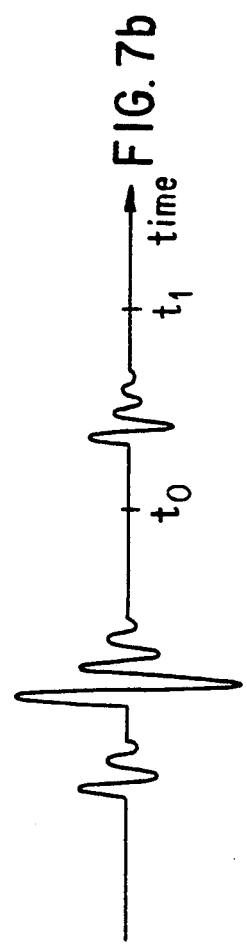
Figure 7C:
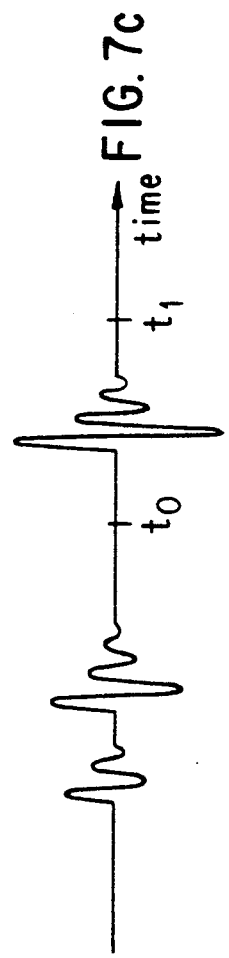
Figure 6A:
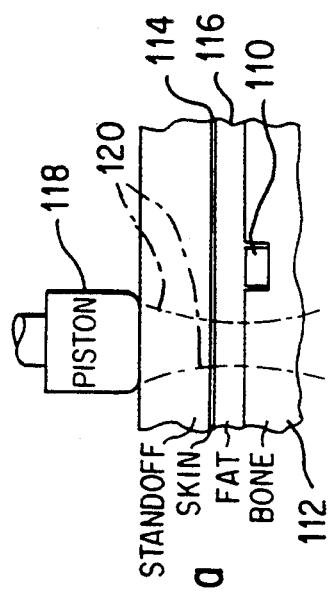
FIG. 6(a), FIG. 6(b), and FIG. 6(c), illustrates different relative positions of a transducer and a target during an ultrasound location method according to an embodiment of the present invention.
Figure 6B:
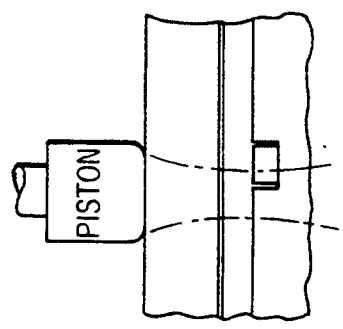
Figure 6C:
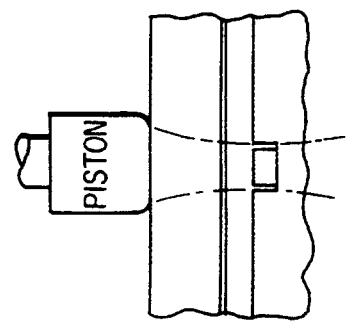

In the present invention as described above in reference to FIG.4, as the signal/position pairs are acquired, the signals are automatically analyzed. The signals are analyzed to detect echoes arising from interfaces between materials of different characteristic acoustic impedance ($Z_0$) as described above. FIG. 6, which includes FIG. 6(a), FIG. 6(b) and FIG. 6(c), illustrates this concept as applied to a low-$Z_0$ target 110 (e.g., a cylindrical fiducial marker) implanted in a high-$Z_0$ material 112 (e.g., the human skull) covered by two layers 114, 116 of low-$Z_0$ material (e.g., scalp and fat). FIG. 6(a), FIG. 6(b) and FIG. 6(c) illustrate the relative position of the transducer piston 118 and the target 110. FIG. 7(a), FIG. 7(b) and FIG. 7(c) illustrate corresponding received reflections of the ultrasound signals for the different relative positions of the transducer piston 118 and target 110 of FIG. 6(a), FIG. 6(b) and FIG. 6(c), respectively. As illustrated, for this case the target interface echo is the echo arising from the interface between the distal surface of the target and the high-$Z_0$ divot in which the target sits. In FIG. 7(a), FIG. 7(b) and FIG. 7(c), the time interval (from $t_0$ to $t_1$) corresponds to the depth of the target interface echo. This time interval is the time interval in which the target interface echo is expected in this example. The reflection signal illustrated in FIG. 7(c) is the signal used to determine the depth of the target from the transducer since it corresponds to the accurate relative positioning of the transducer piston 118 and target 110 illustrated in FIG. 6(c). The computer 26, 54, or 78, for example, extracts the portion of each signal between $t_0$ and $t_1$ and the result is referred to as the windowed signal.

Since the amplitude of the extracted windowed signal is proportional to the proximity of the transducer beam 120 to the center of the target 110, a measure of each windowed signal's amplitude is calculated. For signals whose measured amplitude exceeds a given threshold, the transducer coordinates corresponding to that signal are weighted with that measured amplitude. A centroid is then calculated which estimates the coordinates of the transducer face when it was centered over the target. The signal or signals acquired nearest that centroid are examined and the time index of the leading edge of the target interface echo is detected. Based on the knowledge of the speed of sound in the materials and the geometry of the target, the depth of the target from the transducer face is determined. By adding this depth to the transducer position corresponding to that signal along the orientation of the transducer (also stored along with the signal), the estimated three-dimensional coordinates of the target may be calculated.

As an example, the present invention may be used in image-to-physical space registration for neurosurgical guidance. Once the fiducial markers are implanted in the patient, the preoperative image sets may be acquired. These fiducial markers may be between 1 mm and 10 mm in diameter and are composed of biocompatible materials which are visible in the imaging modalities of interest. The markers are implanted into the skull, flush with the surface of the skull.

Possible marker scenarios include in FIG. 8(a) and FIG. 8(b) a marker 130 in which small cylinders with a thin shell of low-$Z_0$ polymer material filled with a water-based solution, or in FIG. 10 a marker 140 which is identical to marker 130 except that a high-$Z_0$ layer 142 such as a glass marker or "cap" is included on the end of the cylinder which is to be implanted first (i.e., the end of the marker distal to the surface of the skull).

FIG. 9(a) and FIG. 9(b) illustrate expected received echo signals in response to the respective positions of the transducer piston and fiducial marker 130 illustrated in FIG. 8(a) and FIG. 8(b), respectively. The received signal in FIG. 9(b) includes a marker/bone divot echo portion which is not included in the received signal illustrated in FIG. 9(a). This marker/bone divot echo portion is the portion of the signal which is extracted as the windowed signal as discussed above.

As mentioned above, FIG. 10 illustrates a fiducial marker 140 identical to marker 130 except that a high-$Z_0$ layer 142 such as a glass marker "cap" is included on a distal surface of marker 140. FIG. 11 illustrates the expected received signal in response to the transducer piston and fiducial marker 140 arrangement of FIG. 10. The signal illustrated in FIG. 11 includes a marker contents/marker "cap" echo portion which is the portion of the signal extracted as the windowed signal.

In the method of the present invention, each image volume is analyzed to determine the location of the center of each fiducial marker within the three-dimensional coordinate system of the image volume (three or more markers are preferably used in order to more accurately determine coordinate positions). The image volumes and the fiducial locations in each volume are stored on a computer.

Figure 12:
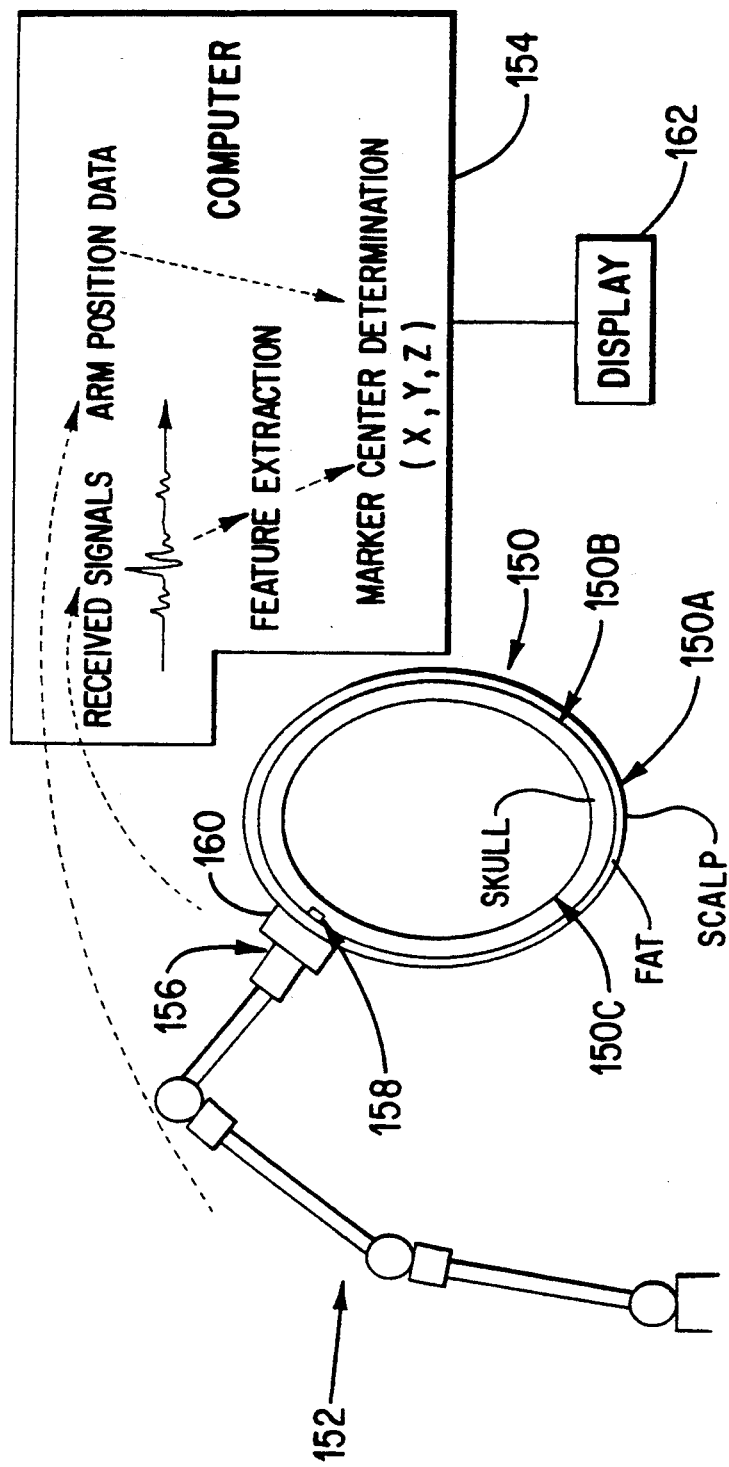
FIG. 12 illustrates an embodiment of the present invention relating to surgical applications thereof.

In the operating room, the patient 150 illustrated in FIG. 12 is fixed in position for surgery, usually with a head clamp. A pointing device such as interactive, image-guided (IIG) arm 152 is connected to a computer 154 holding the image sets and image fiducial locations. An A-mode ultrasound transducer 156 is attached to the pointing device 152. A fiducial marker 158 is implanted below the scalp 150A and subcutaneous fat 150B into the skull 150C of the patient 150. An example of a transducer 156 which may be used in this arrangement is a 10 MHz short-focus piston with a 3 mm-diameter crystal. The pointing device 152 is set up such that the computer 154 continuously calculates the three-dimensional coordinates of the center of the transducer face and the orientation of the transducer. The computer 154 receives the signals from transducer 156 and performs a feature extraction on the received signals in which, for example, the marker/bone divot echo portion or marker contents/marker "cap" echo portion of the signal is extracted. Then computer 154 determines a center position of the marker 158 in response to arm position data received from the pointing device 152 and in response to the feature extraction signal.

In order to implement the present invention, an operator holds the transducer assembly 156 and places it on the scalp 150A of the patient 150 while maintaining contact between the transducer and scalp with acoustic gel and an ultrasonic standoff 160. The operator starts a program within computer 154 that pulses the transducer 156 and receives the reflected signals along with the transducer position information. The operator slowly moves the transducer 156 while signal/position information is collected. The received signals are analyzed to isolate the transducer positions for which the ultrasound beam passes through the marker 158. For space registration purposes, it is the coordinates of the center of the marker 158 which are of interest. As illustrated in FIG. 12, an estimate of the center of the marker 158 may be determined using a centroid/extrapolation process and stored in the computer 154.

This process is repeated until all of the markers (preferably three or more) have been localized. To confirm accuracy of the marker center estimates, the distances between the marker centers are compared to the distances between marker centers as determined from, for example, preoperative images. If the error is within an acceptable range, a transformation is calculated mapping the surgical space coordinates of the pointing device into equivalent locations in the image sets.

The transducer 156 is removed from the pointing device 152, and associated hardware and software are updated via computer 154 to reflect the resulting change in length of the pointing device 152. The surgeon may then point at locations of interest on the patient and look at a display 162 of the computer 154 to see the corresponding location indicated on the preoperative image sets. In this way, accurate, interactive surgical guidance is provided to the surgeon.

Figure 13:
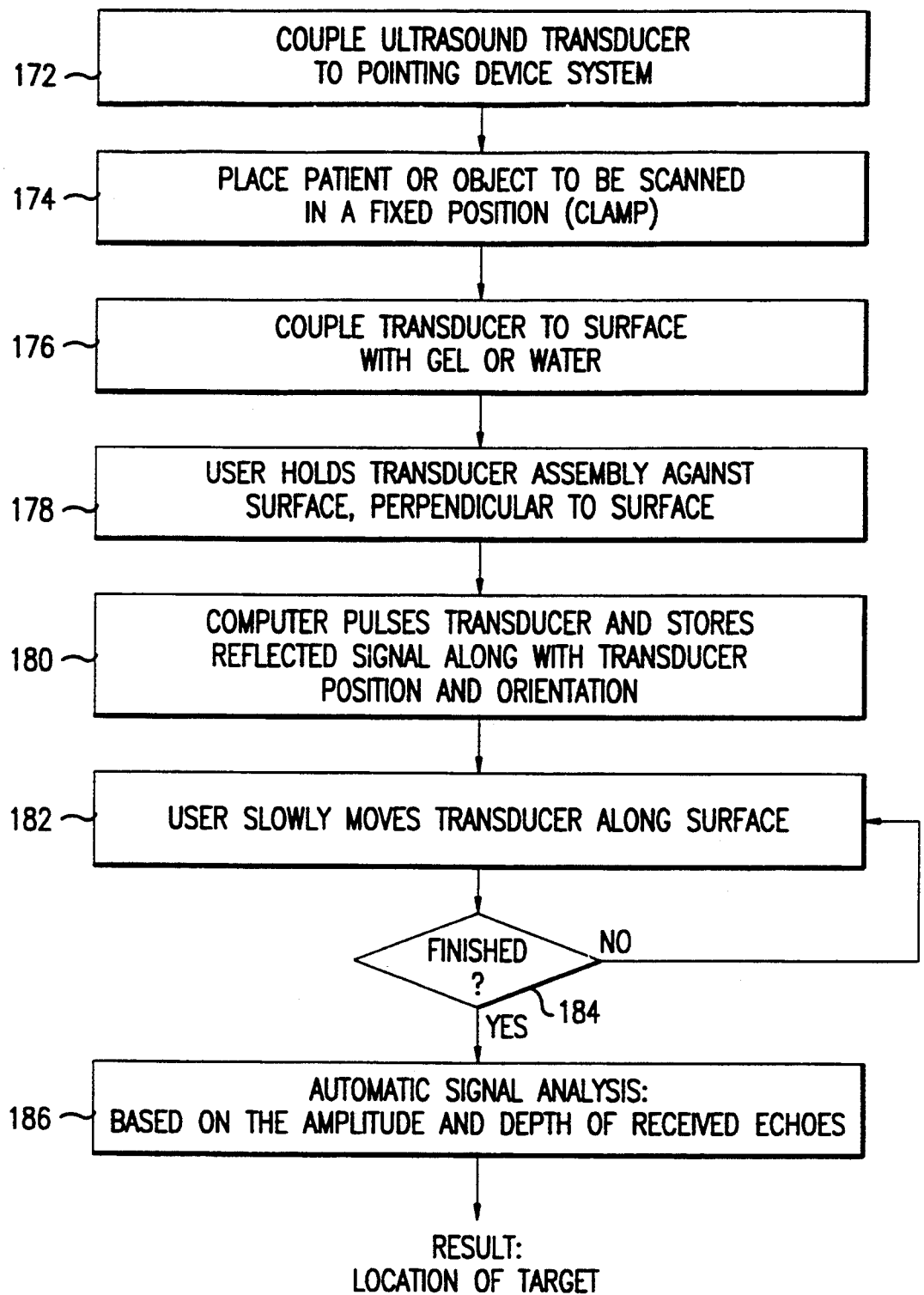
FIG. 13 illustrates a flow chart of an automatic ultrasonic localization method of implanted targets according to an embodiment of the present invention.

FIG. 13 illustrates a flowchart of an ultrasound method of locating implanted targets according to an embodiment of the present invention. In step 172 the ultrasound transducer is coupled to the pointing device system. The patient or object to be scanned is placed in a fixed position, for example, by clamping the patient or object to a table (step 174). In step 176, the transducer is coupled to the surface (for example, the scalp of the patient) with gel or water. The user then holds the transducer assembly against the surface in a manner perpendicular to the surface (step 178). The computer is used to pulse the transducer and store the received reflected signal along with a transducer position and orientation in step 180. In step 182, the user slowly moves the transducer along the surface. A determination is made in step 184 as to whether the user is finished. If the user is not finished, the computer again pulses the transducer and stores the reflected signals in step 180. Once all pulsing and storing of signal information has been finished as determined in step 184, the computer provides an automatic signal analysis in step 186 which is based on the amplitude and depth of received echo signals. As a result, the center position of the target may be accurately determined.

Figure 14:
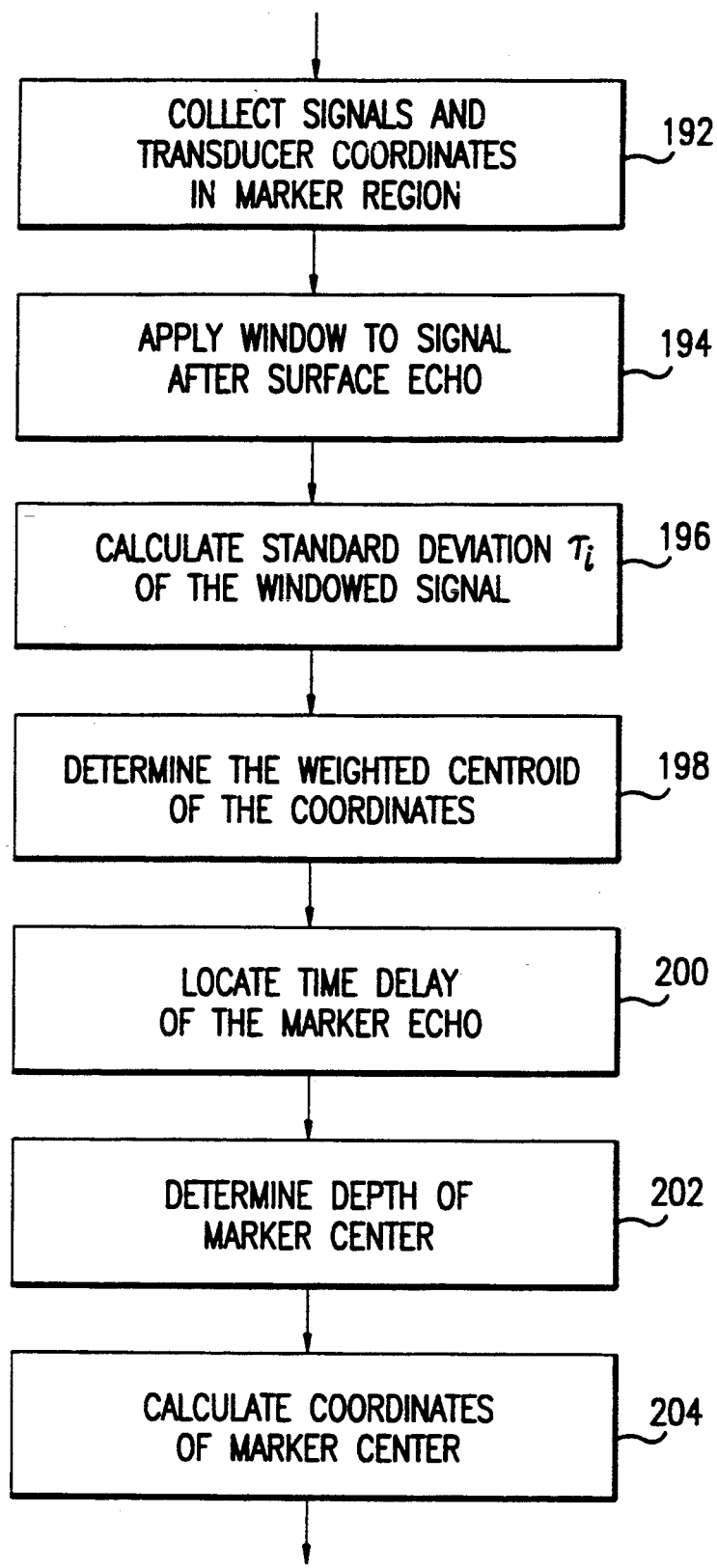
FIG. 14 illustrates one embodiment of an automatic signal analysis determination which may be used in implementing an embodiment of the present invention.

FIG. 14 illustrates one embodiment in which the automatic signal analysis determination of step 186 in FIG. 13 may be implemented. It is noted that other methods of automatic signal analysis may be implemented within the scope and spirit of the present invention and FIG. 14 merely illustrates an embodiment thereof.

FIG. 14 includes a step 192 of collecting signals and transducer coordinates in the marker region, including the reflected ultrasound signals and the ultrasound transducer position data. In order to perform this step, the reflected signals are analyzed to detect echoes arising from interfaces between materials of different acoustic impedance. Such reflected ultrasound signals include, for example, those signals illustrated in FIG. 7(a), FIG. 7(b), FIG. 7(c), FIG. 9(a), FIG. 9(b) and FIG. 11. Step 194 relates to applying a window to the collected signal after a surface echo occurs therein. This window corresponds to the portion between $t_0$ and $t_1$ in FIG. 7(a), FIG. 7(b) and FIG. 7(c). The windowed portion of the signal is extracted from the reflected signal. The amplitude of the extracted windowed signal corresponds to the proximity of the transducer beam to the center of the target. The standard deviation $\sigma_i$ of the windowed signal is calculated in step 196 as an indication of the proximity of the transducer to the center of the target. The weighted centroid of the coordinates of the signal are determined in step 198, for example, according to the following formulas.

$$x_c = \frac{\sum_i x_i (\sigma_i - \text{threshold})}{\sum_i (\sigma_i - \text{threshold})}$$

$$y_c = \frac{\sum_i y_i (\sigma_i - \text{threshold})}{\sum_i (\sigma_i - \text{threshold})}$$

$$z_c = \frac{\sum_i z_i (\sigma_i - \text{threshold})}{\sum_i (\sigma_i - \text{threshold})}$$

in which, $x_i$, $y_i$ and $z_i$ correspond to the ultrasound transducer position data received from the pointing device, signal $\sigma_i$ relates to the standard deviation calculated in step 196. The "threshold" value is calculated based on the maximum standard deviation $\sigma_i$ of a signal which did not pass through the marker. By subtracting this threshold value from each standard deviation value $\sigma_i$, the effect on the centroid calculation of collecting signal/position data outside the marker region is minimized. The coordinates $x_c$, $y_c$ and $z_c$ are the coordinates of the transducer face when it was centered over the target. Together, steps 194, 196 and 198 perform the localization used to determine the lateral position of the center of the marker.

In step 200, a time delay of the marker echo is located nearest the position of the centroid coordinates ($x_c$, $y_c$, $z_c$) to detect the leading edge of the target interface echo. Step 202 determines the depth of the marker center, for example, according to the formula:

$$d_c = d_d - 0.5 * m_h$$

where $d_c$ is the depth from the marker center to the face of the transducer, $d_d$ is the distance from the transducer face to the target interface (e.g., the interface between the marker and the divot in which the marker sits), and $m_h$ is the marker height. The depth of the target from the transducer face may be determined based on the speed of sound in the materials and the geometry of the target. By adding this depth to the transducer position corresponding to that signal along the orientation of the transducer (also stored along with the signal), the estimated three-dimensional coordinates of the target may be calculated. Step 204 calculates the three-dimensional coordinates for the marker center based on the depth of the marker, the determined transducer position, and the ultrasound transducer position data. Steps 200, 202 and 204 together perform depth localization of the marker for determining the depth of the marker from the position of the transducer.

While the signal analysis determination steps illustrated in FIG. 14 have been described as set forth above, it is pointed out that the present invention is not specifically limited to this marker localization method. The present invention could be practiced by locating the position of the target or fiducial marker using another method which accurately determines the position of the marker.

Figure 15:
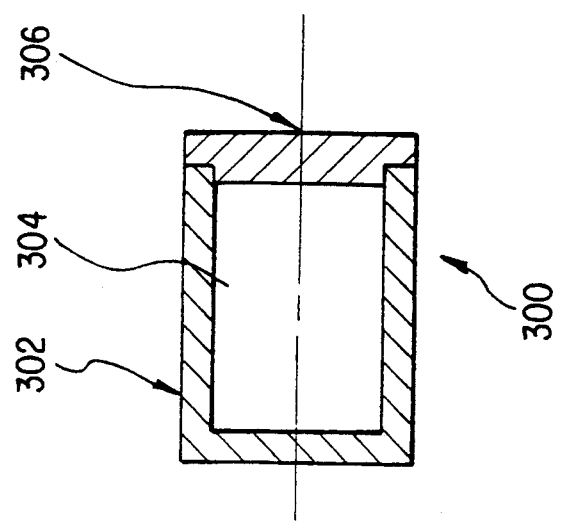
FIG. 15 illustrates a fiducial marker which may be used in implementing an embodiment of the present invention.

FIG. 15 illustrates a fiducial marker 300 which may be used in implementing the present invention. The fiducial marker 300 may be left implanted, for example, entirely beneath the skin for extended periods of time. The marker 300 comprises a cylinder 302 defining a space 304 into which may be placed, for example, one or more imaging agents. A cylindrical shape is preferred for marker 300, because this shape minimizes the size of the incision that must be made for the marker's insertion. It is also the shape that best corresponds to the hole that may be drilled in a bone to accommodate the marker. In any case, it is preferred that the marker at least be symmetrical in shape. The body of the cylinder is sealed off with a cap 306 or is otherwise sealed. The body is preferably constructed of an organic polymer known to be well tolerated by the body for extended periods of time, such as polymethyl methacrylate (PMMA), high density polyethylene, or ceramics such as zirconium oxide and aluminum oxide. The entire marker assembly is small enough for long-term implantation into bone without causing distortion of the bone over time. One exemplary size provides for the marker to be 4 mm in diameter and 3 mm in height. The marker may be implanted in a human skull, flush with the surface of the skull, beneath the fat and subcutaneous fat. Additionally, the cap 306 of the marker may include a high acoustic impedance layer such as a glass marker or "cap" similar to the marker illustrated in FIG. 10.

The cylindrical marker defined above is only one example of possible target composition, geometry and implantation amenable to localization using the present invention. Possible embodiments of implanted targets which may be used to implement the present invention include the following: A low-$Z_0$ target implanted under one or more low-$Z_0$ layers but into a high-$Z_0$ layer, flush with the surface of that layer. The target echo in that case is the interface between the target and the high-$Z_0$ divot in which the target sits. Additional possibilities include a low-$Z_0$ target implanted in high $Z_0$ materials, and a high-$Z_0$ target implanted in a low-$Z_0$ material.

The present invention may be embodied in other specific forms other than that specifically disclosed in this application without departing from its spirit or essential characteristics. For example, while a specific fiducial marker has been described in reference to FIG. 15, the present invention is not limited to localization of this particularly described implanted marker and may be implemented to detect, for example, any implanted target.

What is claimed is:

1. A method for automatically locating a position of a first object in a physical space, comprising steps of:
    attaching a transducer to a coordinate space digitizer having a defined coordinate system in said physical space;
    pulsing said transducer while translating it along a surface of interest near said first object;
    receiving echoes from said pulsed transducer arising from a difference in an acoustic impedance of a first portion of the first object and an acoustic impedance of a material located near said first portion of the first object; and
    determining automatically a coordinate position in said defined coordinate system of said first object in response to said received echoes and a position and orientation of said transducer.

2. A method according to claim 1, wherein said first object is a fiducial marker.

3. A method according to claim 2, wherein said fiducial marker is implanted in a bone.

4. A method according to claim 3, wherein said bone is a skull of a patient and said surface of interest is a scalp of said patient.

5. A method according to claim 1, wherein said material located near said first portion of the first object is a second object having an acoustic impedance different from the acoustic impedance of the first portion of the first object.

6. A method according to claim 1, wherein said material located near said first portion of the first object is a second portion of the first object having an acoustic impedance different from the acoustic impedance of the first portion of the first object.

7. A method according to claim 1, wherein said pulsing and receiving steps are repeated for a plurality of positions and orientations of said transducer and said determining step determines a position of said first object in response to said plurality of receiving steps and said plurality of positions and orientations of said transducer.

8. A method according to claim 1, wherein said determining step further comprises steps of:
   determining automatically a time delay between said received echoes; and
   determining automatically a physical depth of said first object from said transducer.

9. A method according to claim 1, wherein said method determines the coordinate position of the first object in said physical space so that each location in physical space is mapped into a corresponding location in an image volume of said physical space.

10. A method according to claim 9, wherein said physical space to image volume mapping is providing for interactive, image-guide surgery or fractionated radiotherapy.

11. A method according to claim 1, wherein said transducer is an ultrasound transducer.

12. A method according to claim 1, wherein said determining step determines a position of said first object in response to said received echoes, a correspondence between a time delay between received echoes and a physical depth between said first object and said transducer, and a position and orientation of said transducer.

13. A method according to claim 1, further comprising a step of determining a position of said first object in response to said received echoes and a corresponding position and orientation of said transducer which corresponds to a position of said transducer during said pulsing step.

14. A method according to claim 1, wherein said determining step comprises steps of:
   extracting a windowed surface echo signal from said received echoes;
   calculating a standard deviation of said extracted windowed surface echo signal;
   calculating a weighted centroid of positions of said transducer;
   locating a time delay of said windowed surface echo signal nearest the weighted centroid;
   calculating a depth of a center of the first object in response to a depth of an interface in which said first object is located and a height of said first object; and
   calculating coordinates in said coordinate system of the center of the first object in response to said calculated depth and said time delay.

15. A method according to claim 1, wherein said receiving step receives echoes from said pulsed transducer arising from differences in acoustic impedances of said first portion and different portions within said first object.

16. A method according to claim 1, wherein said acoustic impedance of said first portion of said object is lower than said acoustic impedance of said material located near said first portion of said first object.

17. A method according to claim 1, wherein said first object is a symmetric object.

18. A method according to claim 17, wherein said first object is cylindrical in shape.

19. A method for automatic amplitude-mode ultrasound location of an implanted fiducial marker in a physical space, comprising steps of:
   attaching an ultrasound transducer to a coordinate space digitizer having a defined coordinate system in said physical space;
   pulsing said ultrasound transducer while translating it along a surface of interest near said implanted fiducial marker;
   receiving echoes from said pulsed ultrasound transducer arising from a difference in an acoustic impedance of a first portion of the implanted fiducial marker and an acoustic impedance of a material located near said first portion of the implanted fiducial marker; and
   determining automatically a coordinate position in said defined coordinate system of said implanted fiducial marker in response to said received echoes and a position and orientation of said ultrasound transducer.

20. A method according to claim 19, wherein said fiducial marker is implanted in a bone.

21. A method according to claim 20, wherein said bone is a skull of a patient and said surface of interest is a scalp of said patient.

22. A method according to claim 19, wherein said material located near said first portion of the implanted fiducial marker is a material in which said implanted fiducial marker is implanted.

23. A method according to claim 19, wherein said material located near said first portion of the implanted fiducial marker is an object separate from said implanted fiducial marker having an acoustic impedance different from the acoustic impedance of the first portion of the implanted fiducial marker.

24. A method according to claim 19, wherein said material located near said first portion of the implanted fiducial marker is a second portion of the implanted fiducial marker having an acoustic impedance different from the acoustic impedance of the first portion of the implanted fiducial marker.

25. A method according to claim 24, wherein said implanted fiducial marker comprises a marker body enclosing a space, and wherein the second portion of the implanted fiducial marker is a portion of the marker body of said implanted fiducial marker.

26. A method according to claim 25, wherein the acoustic impedance of the portion of the marker body is higher than the acoustic impedance of the first portion of the implanted fiducial marker.

27. A method according to claim 25, wherein said enclosed space contains one or more imaging agents visible in at least one imaging modality.

28. A method according to claim 25, wherein said portion of the marker body is a cap of the marker body, said marker body and cap enclosing said space.

29. A method according to claim 25, wherein said marker body is cylindrical and said portion of the marker body is one end of the cylindrical marker body.

30. A method according to claim 19, wherein said pulsing and receiving steps are repeated for a plurality of positions and orientations of said transducer and said determining step determines a position of said implanted fiducial marker in response to said plurality of receiving steps and said plurality of positions and orientations of said transducer.

31. A method according to claim 19, wherein said determining step further comprises steps of:
   determining a time delay between said received echoes; and
   determining a physical depth of said implanted fiducial marker from said transducer.

32. A method according to claim 19, wherein said method determines the coordinate position of the first object in physical space so that each location in physical space may be mapped into a corresponding location in an image volume of said physical space.

33. A method according to claim 29, wherein said physical space to image volume mapping is provided for interactive, image-guided surgery or fractionated radiotherapy.

34. A method according to claim 19, wherein said determining step determines a position of said implanted fiducial marker in response to said received echoes, a correspondence between a time delay between received echoes and a physical depth between said implanted fiducial marker and said transducer, and a position and orientation of said ultrasound transducer.

35. A method according to claim 19, further comprising a step of determining a position of said implanted fiducial marker in response to said received echoes and a corresponding position and orientation of said transducer which corresponds to a position of said ultrasound transducer during said pulsing step.

36. A method according to claim 19, wherein said determining step comprises steps of:
   extracting a windowed surface echo signal from said received echoes;
   calculating a standard deviation of said extracted windowed surface echo signal;
   calculating a weighted centroid of positions of said ultrasound transducer;
   locating a time delay of said windowed surface echo signal nearest the weighted centroid;
   calculating a depth of a center of the implanted fiducial marker in response to a depth of an interface in which said implanted fiducial marker is located and a height of said implanted fiducial marker; and
   calculating coordinates in said coordinate system of the center of the implanted fiducial marker in response to said calculated depth and said time delay.

37. A method according to claim 19, wherein said receiving step receives echoes from said pulsed ultrasound transducer arising from differences in acoustic impedances of said first portion and different portions within said implanted fiducial marker.

38. A method according to claim 19, wherein said acoustic impedance of said first portion of said implanted fiducial marker is lower than said acoustic impedance of said material located near said implanted fiducial marker.

39. A method according to claim 19, wherein said implanted fiducial marker is a symmetric object.

40. A method according to claim 39, wherein said implanted fiducial marker is cylindrical in shape.

41. A method according to claim 19, wherein said coordinate space digitizer includes a pointing device.

42. A method according to claim 19, wherein said method automatically locates coordinate positions of a plurality of implanted fiducial markers.

43. A method according to claim 42, wherein the method determines the coordinate positions of the plurality of the fiducial markers in physical space, said method further comprising a step of mapping each location in physical space into a corresponding location in an image volume of said physical space in response to the determined coordinate positions of the plurality of fiducial markers.

44. A system for locating a position of a first object in a physical space, comprising:
   a coordinate space digitizer having a defined coordinate system in said physical space;
   an ultrasound transducer connected with said coordinate space digitizer;
   a pulser pulsing said ultrasound transducer while translating it along a surface of interest located near said first object;
   a receiver receiving echoes from said pulsed ultrasound transducer arising from a difference in an acoustic impedance of a first portion of the first object and an acoustic impedance of a material located near said first portion of the first object; and
   means for automatically determining a coordinate position in said defined coordinate system of said first object in response to said received echoes and a position and orientation of said ultrasound transducer.

45. A system according to claim 44, wherein said first object is an implanted fiducial marker.

46. A system according to claim 45, wherein said material is a second object in which said implanted fiducial marker is implanted.

47. A system according to claim 45, said implanted fiducial marker including a housing containing a cavity, said cavity containing said first portion, wherein a second portion of the implanted fiducial marker includes said material located near said first portion.

48. A system according to claim 47, wherein said second portion is one end of the housing of the implanted fiducial marker.

49. A system according to claim 48, wherein said one end of the housing comprises a cap of the housing, said housing and cap enclosing said cavity.

50. A system according to claim 47, wherein said cavity contains one or more imaging agents visible in at least one imaging modality.

51. A fiducial marker assembly comprising an imaging marker assembly including a housing containing a cavity, said imaging marker assembly comprising:
   a first portion including a first material having a first acoustic impedance; and
   a second portion including a second material having a second acoustic impedance which is different than said first acoustic impedance.

52. A fiducial marker assembly according to claim 51, wherein said second portion comprises one end of the housing of said imaging marker assembly.

53. A fiducial marker assembly according to claim 52, wherein said one end of the housing comprises glass.

54. A fiducial marker assembly according to claim 52, wherein said one end of the housing is a cap of the housing, said housing and cap enclosing said cavity.

55. A fiducial marker assembly according to claim 51, wherein said second portion comprises a layer near an end of said fiducial marker.

56. A fiducial marker assembly according to claim 55, wherein said second acoustic impedance is higher than said first acoustic impedance.

57. A fiducial marker assembly according to claim 51, wherein said fiducial marker is a permanent implantable fiducial marker.

58. A fiducial marker assembly according to claim 51, wherein said fiducial marker assembly is for use in an ultrasound detection technique.

59. A fiducial marker assembly according to claim 51, wherein said cavity contains one or more imaging agents visible in at least one imaging modality.

60. A fiducial marker assembly according to claim 51, wherein said first portion is said cavity and said first material is an imaging agent contained in said cavity.

61. A fiducial marker assembly according to claim 60, wherein said second portion is one end of the housing of said imaging marker assembly.

62. A fiducial marker assembly according to claim 61, wherein said one end of the housing is a cap of the housing, said housing and cap enclosing said cavity.

63. A method for automatically locating a position of a fiducial marker implanted in a bone, comprising steps of:
attaching a transducer to a coordinate space digitizer having a defined coordinate system;
pulsing said transducer while translating it along a surface of interest near said fiducial marker;
receiving echoes from said pulsed transducer arising from a difference in an acoustic impedance of a portion of the fiducial marker and an acoustic impedance of a material located near said portion of the fiducial marker; and
determining a position in said defined coordinate system of said fiducial marker in response to said received echoes and a position and orientation of said transducer.

64. A method according to claim 65, wherein said bone is a skull of a patient and said surface of interest is a scalp of said patient.

65. A method for registering a physical space with image volumes including automatically locating a position of an object, comprising steps of:
attaching a transducer to a coordinate space digitizer having a defined coordinate system;
pulsing said transducer while translating it along a surface of interest near said object;
receiving echoes from said pulsed transducer arising from a difference in an acoustic impedance of a portion of the object and an acoustic impedance of a material located near said portion of the object; and
determining a position in said defined coordinate system of said object in response to said received echoes and a position and orientation of said transducer.

66. A method according to claim 65, wherein said method provides said physical space to image volume registration as a tool for interactive, image-guided surgery or fractionated radiotherapy.

67. A method for automatically locating a position of an object, comprising steps of:
attaching a transducer to a coordinate space digitizer having a defined coordinate system;
pulsing said transducer while translating it along a surface of interest near said object;
receiving echoes from said pulsed transducer arising from a difference in an acoustic impedance of a portion of the object and an acoustic impedance of a material located near said portion of the object; and
determining a position in said defined coordinate system of said object in response to said received echoes and a position and orientation of said transducer, wherein said determining step comprises steps of:
extracting a windowed surface echo signal from said received echoes;
calculating a standard deviation of said extracted windowed surface echo signal;
calculating a weighted centroid of positions of said transducer;
locating a time delay of said windowed surface echo signal nearest the weighted centroid;
calculating a depth of a center of the object in response to a depth of an interface in which said object is located and a height of said object; and
calculating coordinates in said coordinate system of the center of the object in response to said calculated depth and said time delay.

68. A method for automatically locating a position of an object, comprising steps of:
attaching a transducer to a coordinate space digitizer having a defined coordinate system;
pulsing said transducer while translating it along a surface of interest near said object;
receiving echoes from said pulsed transducer arising from a difference in an acoustic impedance of a portion of the object and an acoustic impedance of a material located near said portion of the object; and
determining a position in said defined coordinate system of said object in response to said received echoes and a position and orientation of said transducer;
wherein said acoustic impedance of said portion of said object is lower than said acoustic impedance of said material located near said portion of said object.

69. A method for automatic amplitude-mode ultrasound location of a fiducial marker implanted in a bone, comprising steps of:
attaching an ultrasound transducer to a coordinate space digitizer having a defined coordinate system;
pulsing said ultrasound transducer while translating it along a surface of interest near said implanted fiducial marker;
receiving echoes from said pulsed ultrasound transducer arising from a difference in an acoustic impedance of a portion of the implanted fiducial marker and an acoustic impedance of a material located near said portion of the implanted fiducial marker; and
determining a position in said defined coordinate system of said implanted fiducial marker in response to said received echoes and a position and orientation of said ultrasound transducer.

70. A method according to claim 69, wherein said bone is a skull of a patient and said surface of interest is a scalp of said patient.

71. A method for automatic amplitude-mode ultrasound location of an implanted fiducial marker including a marker body and a cap together enclosing a space, comprising steps of:
attaching an ultrasound transducer to a coordinate space digitizer having a defined coordinate system;
pulsing said ultrasound transducer while translating it along a surface of interest near said implanted fiducial marker;
receiving echoes from said pulsed ultrasound transducer arising from a difference in an acoustic impedance of a portion of the implanted fiducial marker and an acoustic impedance of the cap of the implanted fiducial marker; and determining a position in said defined coordinate system of said implanted fiducial marker in response to said received echoes and a position and orientation of said ultrasound transducer.

72. A method according to claim 71, wherein the acoustic impedance of the cap is higher than the acoustic impedance of the portion of the implanted fiducial marker.

73. A method for registering physical space with image volumes including automatic amplitude-mode ultrasound location of an implanted fiducial marker, comprising steps of:

attaching an ultrasound transducer to a coordinate space digitizer having a defined coordinate system;

pulsing said ultrasound transducer while translating it along a surface of interest near said implanted fiducial marker;

receiving echoes from said pulsed ultrasound transducer arising from a difference in an acoustic impedance of a portion of the implanted fiducial marker and an acoustic impedance of a material located near said portion of the implanted fiducial marker; and determining a position in said defined coordinate system of said implanted fiducial marker in response to said received echoes and a position and orientation of said ultrasound transducer.

74. A method according to claim 73, wherein said method provides said physical space to image volume registration as a tool for interactive, image-guided surgery or fractionated radiotherapy.

75. A method for automatic amplitude-mode ultrasound location of an implanted fiducial marker, comprising steps of:

attaching an ultrasound transducer to a coordinate space digitizer having a defined coordinate system;

pulsing said ultrasound transducer while translating it along a surface of interest near said implanted fiducial marker;

receiving echoes from said pulsed ultrasound transducer arising from a difference in an acoustic impedance of a portion of the implanted fiducial marker and an acoustic impedance of a material located near said portion of the implanted fiducial marker; and determining a position in said defined coordinate system of said implanted fiducial marker in response to said received echoes and a position and orientation of said ultrasound transducer, wherein said determining step comprises steps of:

extracting a windowed surface echo signal from said received echoes;

calculating a standard deviation of said extracted windowed surface echo signal;

calculating a weighted centroid of positions of said ultrasound transducer;

locating a time delay of said windowed surface echo signal nearest the weighted centroid;

calculating a depth of a center of the implanted fiducial marker in response to a depth of an interface in which said implanted fiducial marker is located and a height of said implanted fiducial marker; and calculating coordinates in said coordinate system of the center of the implanted fiducial marker in response to said calculated depth and said time delay.

76. A method for automatic amplitude-mode ultrasound location of an implanted fiducial marker, comprising steps of:

attaching an ultrasound transducer to a coordinate space digitizer having a defined coordinate system;

pulsing said ultrasound transducer while translating it along a surface of interest near said implanted fiducial marker;

receiving echoes from said pulsed ultrasound transducer arising from a difference in an acoustic impedance of a portion of the implanted fiducial marker and an acoustic impedance of a material located near said portion of the implanted fiducial marker; and determining a position in said defined coordinate system of said implanted fiducial marker in response to said received echoes and a position and orientation of said ultrasound transducer;

wherein said acoustic impedance of said portion of said implanted fiducial marker is lower than said acoustic impedance of said material located near said portion of said implanted fiducial marker.

77. A system for locating a position of an implanted fiducial marker, said implanted fiducial marker including a housing and a cap, said housing and cap together containing a cavity, said system comprising:

a coordinate space digitizer having a defined coordinate system;

an ultrasound transducer connected with said coordinate space digitizer;

a pulser pulsing said ultrasound transducer while translating it along a surface of interest located near said implanted fiducial marker;

a receiver receiving echoes from said pulsed ultrasound transducer arising from a difference in an acoustic impedance of a portion of the implanted fiducial marker and an acoustic impedance of the cap of the implanted fiducial marker; and means for determining a position in said defined coordinate system of said implanted fiducial marker in response to said received echoes and a position and orientation of said ultrasound transducer.

78. A fiducial marker assembly comprising an imaging marker assembly comprising:

a portion including a material having a first acoustic impedance;

a housing; and a marker cap, said housing and said cap together containing a cavity, said cap having a second acoustic impedance which is different than said first acoustic impedance.

79. A fiducial marker assembly according to claim 78, wherein said cap is a glass marker cap.

80. A fiducial marker assembly comprising an imaging marker assembly having a housing, said housing containing a cavity, comprising:

a first portion including a first material having a first acoustic impedance; and a second portion including a second material having a second acoustic impedance which is different than said first acoustic impedance, said second portion comprising a layer near an end of said fiducial marker;

wherein said second acoustic impedance is higher than said first acoustic impedance.

* * * * *

UNITED STATES PATENT AND TRADEMARK OFFICE
CERTIFICATE OF CORRECTION

PATENT NO. : 5,394,875
DATED : March 7, 1995
INVENTOR(S) : Judith T. Lewis et al It is certified that error appears in the above-indentified patent and that said Letters Patent is hereby corrected as shown below:

Column 13, line 23, change "image-guide" to --image-guided--.

Column 15, line 12, change "claim 29" to --claim 32--.

Column 17, line 32, change "claim 65" to --claim 63--.

Signed and Sealed this

Twentieth Day of June, 1995

Attest:

BRUCE LEHMAN

Attesting Officer        Commissioner of Patents and Trademarks